(12) United States Patent
Erkens et al.

(10) Patent No.: US 10,835,462 B2
(45) Date of Patent: Nov. 17, 2020

(54) BLEACHING AGENT TABLETS

(71) Applicant: Henkel AG & Co. KGaA, Duesseldorf (DE)

(72) Inventors: Udo Erkens, Willich (DE); Torsten Lechner, Langenfeld (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 16/721,676

(22) Filed: Dec. 19, 2019

(65) Prior Publication Data

US 2020/0206105 A1  Jul. 2, 2020

(30) Foreign Application Priority Data

Dec. 28, 2018 (DE) .......... 10 2018 133 688
Sep. 19, 2019 (DE) .......... 10 2019 214 297

(51) Int. Cl.
*A61Q 5/08* (2006.01)
*A61K 8/23* (2006.01)
*A61K 8/73* (2006.01)
*A61K 8/02* (2006.01)

(52) U.S. Cl.
CPC .............. *A61K 8/23* (2013.01); *A61K 8/022* (2013.01); *A61K 8/731* (2013.01); *A61Q 5/08* (2013.01); *A61K 2800/434* (2013.01); *A61K 2800/59* (2013.01)

(58) Field of Classification Search
CPC ... A61Q 5/08; A61K 8/19; A61K 8/23; A61K 8/46; A61K 8/731; A61K 8/02; A61K 2800/731; A61K 8/022; A61K 8/447; A61K 8/0216; A61K 2800/59

USPC ................................. 8/431; 424/62
See application file for complete search history.

(56) References Cited

U.S. PATENT DOCUMENTS

| | | | |
|---|---|---|---|
| 2011/0056508 A1* | 3/2011 | Gross ............. | A61Q 5/08 132/208 |
| 2011/0162671 A1* | 7/2011 | Gross ............. | A61Q 5/08 132/208 |
| 2011/0232669 A1* | 9/2011 | Suenger .......... | A61K 8/44 132/208 |
| 2012/0009134 A1* | 1/2012 | Welz ............... | A61K 8/927 424/62 |
| 2012/0227756 A1* | 9/2012 | Gross ............. | A61K 8/22 132/208 |

FOREIGN PATENT DOCUMENTS

CN          101828550 A       9/2010

* cited by examiner

*Primary Examiner* — Eisa B Elhilo
(74) *Attorney, Agent, or Firm* — Lorenz & Kopf, LLP

(57) ABSTRACT

The present disclosure concerns a bleaching tablet comprising a tablet core and a tablet shell encasing the tablet core, wherein the bleaching tablet—with respect to its weight—contains
a) from about 10% to about 70% by weight of peroxodisulphate(s);
b) from about 1% to about 14% by weight of percarbonate(s);
c) from about 5% to about 15% by weight of disintegrant formed from cellulose-containing material, wherein the percarbonate or the percarbonates are contained in the tablet core. The present disclosure furthermore concerns a method for bleaching human hair.

19 Claims, No Drawings

BLEACHING AGENT TABLETS

CROSS-REFERENCE TO RELATED APPLICATION

This application claims priority to German Patent Application No. 10 2019 214 297.4, filed Sep. 19, 2019 and to German Patent Application No. 10 2018 133 688.8, filed Dec. 28, 2018, which are both incorporated herein by reference in their entirety.

TECHNICAL FIELD

The present disclosure relates to agents for oxidatively changing colour in the field of cosmetics, which are in particular suitable for the lightening of keratinous fibres, in particular human hair.

BACKGROUND

The oxidizing agents contained in bleaching agents are capable of lightening the hair fibre by the oxidative destruction of melanin, the characteristic colorant of hair. For a moderate bleaching effect, it is sufficient to use hydrogen peroxide—optionally with the addition of ammonia or other alkalizing agents—as the oxidizing agent alone; to obtain a stronger bleaching effect, it is usual for a mixture of hydrogen peroxide and peroxodisulphate salts and/or peroxomonosulphate salts to be used.

For reasons of stability, commercially available bleaching agents are usually presented in two preparations which are packaged separately from one another, which are mixed together immediately prior to use to form a ready-to-use preparation. Usually, commercially available bleaching agents include a liquid oxidizing agent preparation and a powder which contains solid oxidizing agents. This bleaching powder suffers from the problem of producing dust during manufacture and when the consumer is mixing it.

Alternatively, instead of the powder, agents in the form of pastes may be mixed with a liquid oxidizing agent preparation. However, dosing of both powders and pastes is often seen by the consumer as troublesome or difficult. While a professional can match the lightening result to a specific hair colour by varying the quantities of powder or paste and oxidizing agent preparation, the consumer mixing it up themselves often finds it difficult to reproduce a desired lightening result exactly later on when applying it again.

In order to minimize these problems, a pre-specified quantity of bleaching agent is desirable. This can be solved by using pre-packaged quantities of powder; however this does not solve the problem of dust when mixing. The tablet dosage form is significantly better suited for this purpose, and in addition is highly acceptable to the consumer.

However, the advantages of a tablet are countered by some disadvantages: because sufficiently stable, i.e. strong, fracture-resistant shaped articles can only be produced by using a relatively high pressing force, this leads to substantial compaction of the components of the shaped article, and consequently to a delayed disintegration of the shaped article.

The problem with highly compacted shaped articles taking too long to disintegrate is known in particular in pharmaceuticals, where specific disintegration aids, known as tablet disintegrants, have been used for a long time in order to shorten the disintegration times. With the aggressive ingredients of bleaching agents, however, the function of the usual disintegrants over long storage periods cannot be sufficiently guaranteed. In addition, the disintegrants in the subsequent ready-to-use mixture must not cause problems as regards viscosity, i.e., they must not act cause thickening.

Handling the oxidizing agent constitutes a further problem. Conventional products use hydrogen peroxide. It is often provided in plastic bottles as a separate component. In order to produce the ready-to-use bleaching agent, therefore, at least two separately provided components, the persulphate and the hydrogen peroxide solution, have to be mixed together. The sustainability-aware consumer sets increasing score by the ecological aspects of a product. One aim in this regard is also to save on packaging material. Products which are used in as concentrated a form as possible, which include only one component and which only have to be mixed with water in order to produce the ready-to-use mixture in an optimized manner, have a distinct advantage having regard to saving on packaging material.

BRIEF SUMMARY

Bleaching tablets that include a tablet core and a tablet shell encasing the table core, and methods of bleaching human hair using the bleaching tablet, are provided herein. In an embodiment, a bleaching tablet that includes a tablet core and a tablet shell encasing the tablet core includes— with respect to its weight:

a) from about 10% to about 70% by weight of peroxodisulphate(s), b) from about 1% to about 14% by weight of percarbonate(s); and c) from about 5% to about 15% by weight of disintegrant formed from cellulose-containing material.

The percarbonate(s) are included in the tablet core.

In another embodiment, a bleaching tablet consists of a tablet core and a tablet shell encasing the tablet core. The bleaching tablet includes—with respect to its weight:

a) from about 25% to about 52.5% by weight of peroxodisulphates, wherein the peroxodisulphates comprise a mixture of potassium peroxodisulphate, ammonium peroxodisulphate, and sodium peroxodisulphate;

b) from about 4% to about 12% by weight of alkali metal, alkaline earth metal or ammonium salt of a percarbonate; and c) from about 5% to about 15% by weight of disintegrant formed from cellulose-containing material, The percarbonate(s) are included in the tablet core and the peroxodisulphates are included in the tablet shell.

In another embodiment, a method for bleaching human hair is provided, in which (a) a bleaching tablet as described above is introduced into a quantity of water, (b) the mixture obtained from (a) is homogenized, and (c) the homogenized mixture from (b) is applied to the human hair.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The objective of the present disclosure is to further improve the application properties of bleaching agents. In this regard, a saving on packaging should be obtained and handling improved.

It has been shown that tablets comprising peroxides as a first component and percarbonates spatially separated therefrom as the second component achieve the objectives mentioned. A further advantage is the greater consumer acceptance, because no dust is formed, portioning is reliable and a saving on packaging is made.

The objective of the present disclosure is achieved by employing the bleaching tablet as contemplated herein. Thus, in a first aspect, the present disclosure provides a bleaching tablet comprising a tablet core and a tablet shell encasing the tablet core, wherein the bleaching tablet—with respect to its weight—contains a) from about 10% to about 70% by weight of peroxodisulphate(s), b) from about 1% to about 14% by weight of percarbonate(s) and c) from about 5% to about 15% by weight of disintegrant formed from cellulose-containing material, wherein the percarbonate or the percarbonates are contained in the tablet core.

The preparations as contemplated herein contain, as the first essential ingredient, from about 10% to about 70% by weight of peroxodisulphate(s), wherein preferred bleaching tablets—with respect to its weight—contain from about 7.5% to about 65% by weight, preferably from about 10% to about 60% by weight, more preferably from about 20% to about 55% by weight, particularly preferably from about 25% to about 52.5% by weight and in particular from about 30% to about 40% by weight of peroxodisulphate(s).

Preferred peroxodisulphates to be used are the alkali- and ammonium peroxodisulphates, in particular sodium peroxodisulphate, potassium peroxodisulphate, ammonium peroxodisulphate and mixtures thereof.

The peroxodisulphates are inorganic salts of a peroxosulphuric acid. Preferred mixtures comprise a mixture of potassium peroxodisulphate and ammonium peroxodisulphate or a mixture of sodium peroxodisulphate and ammonium peroxodisulphate. In accordance with a particularly preferred embodiment of the present disclosure, a bleaching tablet is provided in which the inorganic salt of a peroxosulphuric acid is constituted by a mixture comprising from about 5% to about 40% by weight, preferably from about 10% to about 35% by weight, more preferably from about 15% to about 30% by weight of potassium peroxodisulphate, from about 5% to about 20% by weight, preferably from about 8% to about 18% by weight, more preferably from about 10% to about 15% by weight of ammonium peroxodisulphate and/ or from 0 to about 10% by weight, preferably from about 1% to about 9% by weight, more preferably from about 2% to about 8.5% by weight, of sodium peroxodisulphate, respectively with respect to the total weight of the bleaching tablet.

Extremely preferably, the quantity of potassium peroxodisulphate is always kept higher than the quantity of any optionally employed sodium peroxodisulphate and ammonium peroxodisulphate. Furthermore, a specific ratio of potassium peroxodisulphate to sodium peroxodisulphate has been shown to be particularly suitable for obtaining stable tablets which disintegrate rapidly.

The peroxodisulphate is preferably located in the outer portion of the tablet, i.e. in the tablet shell. In bleaching tablets which are preferred as contemplated herein, the ratio by weight of the potassium peroxodisulphate contained in the agent to the total quantity of the peroxodisulphates contained in the agent is at least about 0.2, preferably at least about 0.3, more preferably at least about 0.4, particularly preferably at least about 0.5 and in particular at least about 0.6.

The bleaching tablets as contemplated herein contain one or more percarbonates as the second ingredient.

As a rule, percarbonates and salts of peroxosulphuric acids which are suitable for the bleaching tablet are solids. Preferably, the percarbonate and the salt of the peroxosulphuric acid which are used in the bleaching tablet as contemplated herein are solids.

The fact that the bleaching tablet includes only one piece ensures that the bleaching tablet is easy to handle and can be reliably dosed. The percarbonate which is used and the salt of the peroxosulphuric acid which is used do not produce dust, because they are compressed into a tablet. The tablet core in the cosmetic agent as contemplated herein forms an enclosed space. This ensures that the percarbonate does not come into contact with water and produce gases.

The bleaching tablet as contemplated herein is used for the oxidative lightening of human hair. The term "oxidative lightening" should be understood to mean bleaching agents and also agents for lightening keratinous fibres, which contain the percarbonate and the salt of the peroxosulphuric acid. If pure bleaching or lightening is to be carried out, then the cosmetic agent does not contain any further colorants. However, it may also be desirable to provide the keratinous fibres with nuances in addition to bleaching/lightening. For the purposes of providing nuances, the bleaching tablet as contemplated herein may additionally also contain colouring components such as, for example, direct dyes and/or oxidation dye precursors. The preferred intended use for the bleaching tablet is in fact bleaching or lightening, and therefore the bleaching tablet preferably contains either no colorants or contains them in only small quantities which are suitable for providing a slight nuance.

As contemplated herein, the percarbonate acts as a replacement for hydrogen peroxide. Because the components of the bleaching tablet comprising the percarbonate are mixed together, hydrogen peroxide is generated for bleaching the hair.

In accordance with a preferred embodiment of the present disclosure, the bleaching tablet contains a bleaching agent composition, in which the at least one percarbonate constitutes an alkali metal, alkaline earth metal or ammonium salt of a percarbonate, in particular sodium percarbonate.

As contemplated herein, the at least one percarbonate, in particular sodium percarbonate, is present in the bleaching tablet in a total quantity of from about 4% to about 12% by weight, preferably from about 6% to about 10% by weight with respect to the total weight of the bleaching tablet. This produces the best results having regard to completely replacing liquid hydrogen peroxide as the oxidizing agent.

The term "percarbonate" should preferably be understood to mean an $H_2O_2$ adduct. The term "sodium percarbonate" as used in the context of the present disclosure should be understood to mean the adduct (or the complex) formed from sodium carbonate and hydrogen peroxide with the composition 2 $Na_2CO_3 \times 3$ $H_2O_2$. Sodium percarbonate forms a white, water-soluble powder which formally decomposes in contact with water into sodium carbonate and hydrogen peroxide. The sodium percarbonate as contemplated herein (2 $Na_2CO_3 \times 3$ $H_2O_2$) has a molar mass of 314.02 g/mol and has the CAS number 15630-89-4.

Sodium percarbonate is commercially available from a variety of providers in different grades of purity. As an example, Evonik Degussa provides a sodium percarbonate with a purity of 98.8% by weight. All of the quantities given above are with respect to 100% sodium percarbonate. When using sodium percarbonate in lower grades of purity, the quantities used have to be recalculated appropriately.

In analogous manner, the term "potassium percarbonate" as used in the context of the present disclosure means the adduct (or the complex) formed by potassium carbonate and hydrogen peroxide with the composition 2 $K_2CO_3 \times 3\ H_2O_2$.

The use of sodium percarbonate has been shown to be particularly suitable in solving the task of the present disclosure.

It has been shown that damage to the hair can be reduced when smaller quantities of percarbonates are used in the bleaching tablet than has been conventionally used. The studies leading to this present disclosure have shown that a further increase in the quantity of percarbonate to more than about 14% by weight does indeed increase the damage to the hair, but does not result in any further strengthening of the lightening. In this connection, it has been shown to be preferable to use the percarbonate in the preferred ranges of quantities. The best lightening power with the comparatively lowest damage to the hair was obtained when the cosmetic agent contained the percarbonates (in particular sodium percarbonate) in a total quantity of from about 6% to about 10% by weight.

All data given as a % by weight as used in the context of the present disclosure are with respect to the total weight of the bleaching tablet. When a mixture of sodium percarbonate and potassium percarbonate is used, the data given as a % by weight are obviously with respect to the sum of the percentages by weight. Clearly, this is also the case for the salts of the peroxosulphuric acids.

The bleaching tablets as contemplated herein contain from about 5 to about 15% by weight of disintegrant formed from cellulose-containing material as the third essential ingredient.

In this regard, before mixing it with the other ingredients, i.e. the ingredients a) and b), the cellulose-containing material is compacted. The expression "compacting" as used here means exerting a pressure on the cellulose-containing material which reduces the volume of the cellulose-containing material without destroying the fibres. Thus, the particles are deformed during compacting, in contrast to aggregation, which simply means deposition of the particles without any essential change to their shape. In this context, compacting in this context should be carried out prior to admixing the disintegrant produced in this manner with the ingredients. Thus, when the pellet comes into contact with water or other liquid, the cellulose-containing material springs out of its compacted state back into a state with an open, loose volume.

In the context of the present disclosure, "compacting" may be a granulation or extrusion; preferably, the compacting is roller compaction, during which the cellulose-containing material is fed to two rollers with their axes of rotational parallel to each other and which turn in opposite directions in order to compact it upon running through the rollers.

The compaction produces granulate particles from the starting material during or after compaction, which form larger aggregates from a plurality of initial particles. These larger aggregates, i.e. the granulate particles, are mixed with the ingredients and the mixture is compressed into pellets.

After the compaction procedure, die compacted granulate should have a density of from about 0.3 to about 1.5 g/cm³. This on the one hand produces a sufficient disintegration action, and on the other hand this range ensures that a chemical deactivation of the disintegrant due to the aggressive components of the tablet does not occur. Furthermore, the oils which are usually incompatible with disintegrants can be contained in the tablets without physical loss of effectiveness—this is not the case with conventional disintegrants.

The "cellulose-containing materials" to be used as contemplated herein as disintegrants are preferably those in which the cellulose present is at least substantially chemically unchanged. A particle size of from about 40-60 µm for the starting material, which is present in larger granulate particles following compacting, has been shown to be advantageous. Ultra-finely dispersed cellulose-containing starting materials with this granulometry can be produced by further, still acceptable comminution effort and in practice do not lead to subsequent problems regarding the viscosity or transparency of the ready-to-use mixture.

The compacted particles of the cellulose-containing material may have a particle size of from about 0.2 to about 6.0 mm, in particular or from about 0.3 to about 1.5 mm, wherein the most appropriate particle size is also dependent on the size of the pellet.

The dispersion properties of the cellulose-containing material may be improved when it is at least partially fibrillated, Le, has been comminuted to bundles each of just a few parallel cellulose fibres.

During the course of the development studies, in particular, two types of cellulose-containing material have been shown to be excellent, namely TMP (=Thermo Mechanical Pulp) and CTMP (=Chemo Thermo Mechanical Pulp). These are two types of what are known as mechanical pulp. In the TMP process, wood chips are fibrillated under steam pressure at approximately 130° C. in pressure refiners to form TMP. When chemicals are used in the wood chip pre-steaming process, CTMP is produced. With the mechanical pulps TMP and CTMP, a certain amount of leaching of the material occurs, but the lignins, resins and other wood components are not completely removed, in particular not as completely as with cellulose production. Thus, these mechanical pulps are cellulose-containing materials which have retained some of the character of the wood.

Particularly preferred bleaching tablets as contemplated herein contain from about 6% to about 14% by weight, preferably from about 8% to about 12% by weight, more preferably from about 5% to about 12.5% by weight, particularly preferably from about 6% to about 11% by weight and in particular from about 7.5% to about 10% by weight of disintegrant formed from cellulose-containing material, wherein preferably, more than about 70% by weight, advantageously more than about 80% by weight, more preferably more than about 90% by weight and in particular more than about 99% by weight of the compacted granulate of the cellulose-containing material has a particle size of from about 0.2 to about 6.0 mm, preferably of from about 0.4 to about 1.5 mm.

Further preferred bleaching tablets as contemplated herein contain from about 6% to about 14% by weight, preferably from about 8% to about 12% by weight, more preferably from about 5% to about 12.5% by weight, particularly preferably from about 6% to about 11% by weight and in particular from about 7.5% to about 10% by weight of disintegrant formed from cellulose-containing material, wherein the particle size of the cellulose-containing starting material is from about 20 to about 200 µm, preferably from about 40 µm to about 60 µm. Arbocel TF 30 HG white from JRS Rettenmaier has been shown to be a particularly preferred product.

The bleaching tablets as contemplated herein may contain alkalizing agents. Examples of preferred alkalizing agents are ammonia, alkanolamine, basic amino acids, as well as inorganic alkalizing agents such as alkali (alkaline earth) metal hydroxides, alkali (alkaline earth) metal metasilicates, alkali (alkaline earth) metal silicates, alkali (alkaline earth)

metal phosphates, alkali (alkaline earth) metal metaphosphates and alkali (alkaline earth) metal hydrogen phosphates. Preferably, the metal ions are lithium, sodium and/or potassium.

inorganic alkalizing agents for use as contemplated herein are preferably selected from calcium hydroxide, barium hydroxide, sodium phosphate, sodium hexametaphosphate, potassium phosphate, sodium silicate, potassium silicate, sodium metasilicate, potassium metasilicate, magnesium silicate, sodium carbonate and potassium carbonate. Sodium silicate, sodium metasilicate and/or sodium hexametaphosphate are particularly preferred.

Alkalizing agents which may be used as contemplated herein are preferably selected from alkanolamines formed from primary, secondary or tertiary amines with a $C_2$-$C_6$ alkyl base unit, which carries at least one hydroxy group. Particularly preferred alkanolamines are selected from the group which is formed by 2-aminoethan-1-ol (monoethanolamine), 3-aminopropan-1-ol, 4-aminobutan-1-ol, 5-aminopentan-1-ol, 1-aminopropan-2-ol (monoisopropanolamine), 1-aminobutan-2-ol, 1-aminopentan-2-ol, 1-aminopentan-3-ol, 1-aminopentan-4-ol, 2-amino-2-methyl-propanol, 2-amino-2-methylbutanol, 3-amino-2-methylpropan-1-ol, 1-amino-2-methylpropan-2-ol, 3-aminopropan-1,2-diol, 2-amino-2-methylpropan-1,3-diol, 2-amino-2-ethyl-1,3-propanediol, N, N-dimethyl-ethanolamine, methylglucamine, triethanolamine, diethanolamine and triisopropanolamine.

The basic amino acids which may be used as alkalizing agents as contemplated herein are preferably selected from the group which is formed by L-arginine, D-arginine, D/L-arginine, L-lysine, D-lysine, D/L-lysine, L-ornithine, D-ornithine, D/L-ornithine, L-histidine, D-histidine and/or D/L-histidine. Particularly preferably, L-arginine, D-arginine and/or D/L-arginine is used as an alkalizing agent in the context of the present disclosure.

When the ready-to-use mixtures contain alkalizing agents, preparations as contemplated herein are preferred which contain the alkalizing agents in a quantity of from about 1% to about 70% by weight, in particular of from about 10% to about 40% by weight, respectively with respect to the total weight of the ready-to-use agent.

The compositions as contemplated herein may additionally contain at least one further bleaching booster which differs from the inorganic peroxy salts.

Compounds which generate aliphatic peroxycarboxylic acids preferably containing 1 to 10 C atoms, in particular 2 to 4 C atoms, and/or optionally substituted peroxy benzoic acids under perhydrolysis conditions may be used as the bleaching boosters. Substances which carry 0- and/or N-acyl groups with the specified number of C atoms and/or optionally substituted benzoyl groups are suitable. Multiply acylated alkylene diamines in particular tetraacetyl ethylenediamine (TAED), acylated triazine derivatives, in particular 1,5-diacetyl-2,4-dioxohexahydro-1,3,5-triazine (DADHT), acylated glycourils, in particular tetraacetyl glycoluril (TAGU), N-acylimides, in particular N-nonanoyl succinimide (NOSI), acylated phenol sulphonates, in particular n-nonanoyl- or isononanoyl oxybenzosulphonate (n- or iso-NOBS), carboxylic acid anhydrides, in particular phthalic acid anhydride, acylated polyalcohols, in particular triacetin, ethylene glycol diacetate and 2,5-diacetoxy-2,5-dihydrofuran are preferred.

Cosmetic oils can be categorized into volatile and non-volatile oils. The term "non-volatile oils" means those oils which have a vapour pressure of less than about 2.66 Pa (about 0.02 mm Hg) at 20° C. and at an atmospheric pressure of 1013 hPa. The term "volatile oils" means those oils which have a vapour pressure of from about 2.66 Pa-40000 Pa (from about 0.02 mm-300 mm Hg), preferably from about 10-12000 Pa (from about 0.1-90 mm Hg), particularly preferably from about 13-3000 Pa, extremely preferably from about 15-500 Pa at 20° C., and at an atmospheric pressure of 1013 hPa.

Volatile cosmetic oils are usually selected from cyclic silicone oils with the INCI name Cyclomethicone. The INCI name Cyclomethicone should in particular be understood to mean cyclotrisiloxane (hexamethylcyclotrisiloxane), cyclotetrasiloxane (octamethylcyclotetrasiloxane), cyclopentasiloxane (decamethylcyclopentasiloxane) and cyclohexasiloxane (dodecamethylcyclohexasiloxane). These oils have a vapour pressure of approximately 13-15 Pa at 20° C.

A cyclomethicone substitute which is more preferred for with the present disclosure is a mixture of $C_{13}$-$C_{16}$ isoparaffins, $C_{12}$-$C_{14}$ isoparaffins and $C_{13}$-$C_{15}$ alkanes, with a viscosity at 25° C. in the range from about 2 to about 6 mPas and which have a vapour pressure at 20° C. in the range from about 10 to about 150 Pa, preferably from about 100 to about 150 Pa. A mixture of this type is, for example, available under the trade name SiClone SR-5 from Presperse Inc. Other preferred volatile silicone oils are selected from volatile linear silicone oils, in particular volatile linear silicone oils containing from about 2-10 siloxane units, such as hexamethyldisiloxane ($L_2$), octamethyltrisiloxane ($L_3$), decamethyltetrasiloxane ($L_4$), as contained, for example, in the commercially available products DC 2-1184, Dow Corning® 200 (0.65 cSt) and Dow Corning® 200 (1.5 cSt) from Dow Corning, and low molecular weight phenyl trimethicone with a vapour pressure at 20° C. of approximately 2000 Pa, such as that available from GE Bayer Silicones/Momentive with the name Baysilone Fluid PD 5.

Further preferred products as contemplated herein contain at least one volatile non-silicone oil. Preferred volatile non-silicone oils are selected from $C_8$-$C_{16}$ isoparaffins, in particular from isononane, isodecane, isoundecane, isododecane, isotridecane, isotetradecane, isopentadecane and isohexadecane, as well as mixtures thereof. $C_{10}$-$C_{13}$-isoparaffin mixtures, in particular those with a vapour pressure at 20° C. of from about 10-400 Pa, preferably from about 13-100 Pa, are preferred.

Further particularly preferred cosmetic oils as contemplated herein are esters of linear or branched, saturated or unsaturated fatty alcohols containing from about 2-30 carbon atoms with linear or branched, saturated or unsaturated fatty acids containing from about 2-30 carbon atoms, which may be hydroxylated. Esters of linear or branched saturated fatty alcohols containing from about 2-5 carbon atoms with linear or branched, saturated or unsaturated fatty acids containing from about 10-18 carbon atoms, which may be hydroxylated, are preferred. Preferred examples in this regard are isopropyl palmitate, isopropyl stearate, isopropyl myristate, 2-hexyldecyl stearate, 2-hexyldecyl laurate, isodecyl neopentanoate, isononyl isononanoate, 2-ethylhexyl palmitate and 2-ethylhexyl stearate. Isopropyl isostearate, isopropyl oleate, isooctyl stearate, isononyl stearate, isocetyl stearate, isononyl isononanoate, isotridecyl isononanoate, cetearyl isononanoate, 2-ethylhexyl laurate, 2-ethylhexyl isostearate, 2-ethylhexyl cocoate, 2-octyldodecyl palmitate, butyloctanoic acid 2-butyloctanoate, diisotridecyl acetate, n-butyl stearate, n-hexyl laurate, n-decyl oleate, oleyl oleate, oleyl erucate, erucyl oleate, erucyl erucate, ethylene glycol dioleate, ethylene glycol dipalmitate. n-hexyl laurate, n-decyl oleate, oleyl oleate, oleyl erucate, erucyl oleate, $C_{12}$-$C_{15}$-alkyl lactate and di-$C_{12}$-$C_{13}$-alkyl malate as well as the benzoic acid esters of linear or branched $C_{8-22}$ alkanols are also preferred. Benzoic acid $C_{12}$-$C_{15}$ alkyl esters, obtainable, for example, as the commercially available product Finsolv® TN ($C_{12}$-$C_{15}$-alkyl benzoate), as well as benzoic acid isostearyl esters obtainable, for example, as Finsolv® SB, 2-ethylhexyl benzoate obtainable, for example, as Finsolv® EB, and benzoic acid 2-octyldodecyl ester obtainable, for example, as Finsolv® BOD, are particularly preferred.

The use of isopropyl esters of $C_{12}$-$C_{18}$ carboxylic acids, in particular the use of isopropyl myristate, and particularly preferably mixtures of isopropyl myristate with $C_{10}$-$C_{13}$ isoparaffin mixtures, the latter preferably with a vapour pressure at 20° C. of from about 10-400 Pa, have been shown to be particularly advantageous.

A further particularly preferred ester oil is triethyl citrate. Further preferred products as contemplated herein contain triethyl citrate and at least one $C_8$-$C_{16}$-isoparaffi, selected from isononane, isodecane, isoundecane, isododecane, isotridecane, isotetradecane, isopentadecane and isohexadecane, as well as mixtures of these isoparaffins. Further preferred products as contemplated herein contain triethyl citrate and at least one $C_8$-$C_{16}$-isoparaffin selected from isononane, isodecane, isoundecane, isododecane, isotridecane as well mixtures of these $C_8$-$C_{16}$-isoparaffins. Further preferred products as contemplated herein contain triethyl citrate and a mixture of isodecane, isoundecane, isododecane and isotridecane.

The expression "triglyceride" as used below means "glycerin triester". Further preferred non-volatile oils as contemplated herein are selected from the triglycerides of linear or branched, saturated or unsaturated, optionally hydroxylated $C_{8-30}$ fatty acids, as long as these are liquid under normal conditions. The use of natural oils such as soya oil, cotton seed oil, sunflower oil, palm oil, palm kernel oil, linseed oil, almond oil, castor oil, corn oil, rapeseed oil, olive oil, sesame oil, thistle oil, wheatgerm oil, peach kernel oil and the liquid fractions of coconut oil and the like may be particularly suitable. Synthetic triglyceride oils are particularly preferable, in particular Capric/Caprylic Triglycerides, for example the commercially available products Myritol® 318 or Myritol® 331 (BASF/Cognis) with unbranched fatty acid residues, as well as glyceryl triisostearate and glyceryl tri(2-ethylhexanoate) with branched fatty acid residues. Triglyceride oils of this type are preferably present in a proportion of less than about 50% by weight with respect to the total weight of all of the cosmetic oils in the product as contemplated herein.

Further particularly preferred non-volatile non-silicone oils as contemplated herein are selected from the dicarboxylic acid esters of linear or branched $C_2$-$C_{10}$ alkanols, in particular diisopropyl adipate, di-n-butyl adipate, di-(2-ethylhexyl) adipate, dioctyl adipate, diethyl-/di-n-butyl/dioctyl sebacate, diisopropyl sebacate, dioctyl malate, dioctyl malate, dicaprylyl malate, diisooctyl succinate, di-2-ethylhexyl succinate and di-(2-hexyldecyl) succinate.

Further particularly preferred non-volatile non-silicone oils as contemplated herein are selected from the symmetrical, unsymmetrical or cyclic esters of carbonic acids with $C_6$-$C_{20}$ alcohols, for example di-n-caprylyl carbonate (Cetiol® CC) or di-(2-ethylhexyl) carbonate (Tegosoft DEC). In contrast, esters of carbonic acid with $C_1$-$C_5$ alcohols, for example glycerin carbonate or propylene carbonate, are not suitable compounds for use as a cosmetic oil.

Further oils which may be preferred as contemplated herein are selected from the esters of dimers of unsaturated $C_{12}$-$C_{22}$ fatty acids (dimeric fatty acids) with monovalent linear, branched or cyclic $C_2$-$C_{15}$ alkanols or with multivalent linear or branched $C_2$-$C_6$ alkanols. Particularly preferably, the total weight of dimeric fatty acid esters is from about 0.5-10% by weight, preferably from about 1-5% by weight, respectively with respect to the weight of the entire water-in-oil emulsion, without taking the weight of the propellant into account.

Further cosmetic oils which are particularly preferred as contemplated herein are selected from non-volatile silicone oils. Preferred non-volatile silicone oils as contemplated herein are selected from linear polyalkylsiloxanes with a kinematic viscosity at 25° C. of at least from about 5 cSt to about 2000 cSt, in particular selected from linear polyalkylsiloxanes with a kinematic viscosity at 25° C. of from about 5 cSt to about 2000 cSt, preferably from about 1.0 to about 350 cSt, particularly preferably from about 50-100 cSt, as obtainable, for example, from Dow Corning or Xiameter under the trade name Dow Corning® 200 or Xiameter PMX. Further preferred non-volatile silicone oils are phenyl trimethicones with a kinematic viscosity at 25° C. of from about 10 to about 100 cSt, preferably of from about 15-30 cSt, as well as cetyl dimethicone.

Preferred agents as contemplated herein contain at least one non-volatile silicone oil which is preferably selected from linear polyalkylsiloxanes with a kinematic viscosity at 25° C. of from about 5 cSt-2000 cSt, preferably from about 10-350 cSt, particularly preferably from about 50-100 cSt, in particular selected from linear polydimethylsiloxanes with a kinematic viscosity at 25° C. of from about 5 cSt-2000 cSt, preferably from about 10-350 cSt, particularly preferably from about 50-100 cSt, in a total quantity of from about 0.1-30% by weight, preferably from about 1-24% by weight, particularly preferably from about 2-18% by weight, extremely preferably from about 4-10% by weight, respectively with respect to the weight of the agent as a whole.

Paraffin oils are also suitable oils for the tablets as contemplated herein. The term "paraffin oils" should be understood to mean mixtures of saturated aliphatic hydrocarbons which are liquid at room temperature. Preferred agents as contemplated herein thus contain at least one paraffin oil.

Some of said oils have been shown to be particularly suitable, because they guarantee the physical and chemical stability of the bleaching tablets over long periods of time and are extremely compatible with the other ingredients of the present disclosure. Preferred bleaching tablets as contemplated herein contain from about 2.5% to about 17.5% by weight, preferably from about 3.5% to about 15% by weight, more preferably from about 5% to about 12.5% by weight, particularly preferably from about 6% to about 11% by weight and in particular from about 7.5% to about 10% by weight of oil(s) from the group formed by paraffin oil, polyisobutene, alkyl benzoates, isopropyl palmitate, isohexadecane, isododecane, and isononyl isononanoate.

Further preferred bleaching tablets as contemplated herein contain from about 2.5% to about 17.5% by weight, preferably from about 3.5% to about 15% by weight, more preferably from about 5% to about 12.5% by weight, particularly preferably from about 6% to about 11% by weight and in particular from about 7.5% to about 10% by weight of paraffin oil.

The objective at the basis of the present disclosure is also achieved by the method for bleaching hair as contemplated herein. Thus, in a second aspect, the present disclosure concerns a method for bleaching human hair, in which (a) the cosmetic agent according to the first aspect of the present disclosure is introduced into a quantity of water, (b) the mixture obtained from (a) is homogenized, and (c) the homogenized mixture from (b) is applied to the human hair.

The agents as contemplated herein are used in a method for lightening keratinous fibres, in particular human hair, in which the agent is applied to the keratin-containing fibres at a temperature from room temperature to about 45° C., is left on the fibres for a treatment time of from about 10 to about 60 minutes and subsequently is rinsed out with water or is washed out with shampoo.

Preferably, the treatment time for the ready-to-use lightening agent is from about 10 to about 60 min, in particular from about 15 to about 50 min, particularly preferably from about 20 to about 45 min. During the treatment time for the agent on the fibre, it may be advantageous to promote the lightening process by supplying heat. The heat may be supplied via an external heat source, such as with the aid of a warm air blower, and also, in particular when lightening the hair of volunteers who are alive, by the body temperature of the volunteers. In the latter case, the part to be lightened is usually covered with a hood. A treatment phase at room temperature is also as contemplated herein. Preferably, the temperature during the treatment time is between about 20° C. and about 40° C., in particular between about 25° C. and about 38° C. The lightening agents generate good bleaching and lightening results even at physiologically acceptable temperatures of below about 45° C.

At the end of the treatment time, the remaining lightening preparation is rinsed out of the hair with water or a cleansing agent. In this regard, in particular, a standard shampoo may be used as the cleansing agent, wherein in particular, the cleansing agent can be dispensed with and the rinsing process may be carried out with tap water when the lightening agent contains a support containing a lot of surfactant.

The description of the preferred embodiments in respect of the first aspect of the present disclosure are also applicable mutatis mutandis to the second aspect of the present disclosure.

Compressed tablet areas in the range from about 5 to about 40 cm² have been shown to be particularly suitable for tablet production, wherein areas of from about 6 to about 35 cm², preferably of from about 7 to about 30 cm², more preferably of from about 8 to about 25 cm² and in particular of from about 9 to about 15 cm² are extremely preferred.

Particularly preferred pressing forces in this regard are in the range from about 1.2 to about 4.5 kN cm$^{-2}$.

The description of the preferred embodiments in respect of the first aspect of the present disclosure are also applicable mutatis mutandis to the third aspect of the present disclosure.

EXAMPLES

1. Bleaching Tablet Formulations
(data as % by weight unless stated otherwise)

|  | KM 1 |
|---|---|
| Magnesium carbonate (heavy) | 2.6 |
| Britesil C 265 | 10 |
| Carboxymethylcellulose (Cekol 50000) | 9.2 |
| Hydroxyethylcellulose (Tylose H 100000 YP 2) | 2.3 |
| Xanthan Gum (Keltrol CG-SFT) | 3.7 |
| EDETA BX Powder | 1.6 |
| Sodium persulphate | 6 |
| Ammonium persulphate + 0.5% silica | 14 |
| Potassium persulphate | 27.4 |
| NaCl | 0.5 |

-continued

|  | KM 1 |
|---|---|
| Dimethicone/dimethiconol | 2.4 |
| Fragrance | 0.3 |
| Arbocel TF 30 HG white | |
| Tablet core: | |
| Sodium percarbonate | 10 |

Firstly, the tablet core was pressed. Next, the tablet shell was pressed around it. The tablets and water were mixed together in a ratio by weight of about 1:2 and then used.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A bleaching tablet comprising a tablet core and a tablet shell encasing the tablet core, wherein the bleaching tablet—with respect to its weight—comprises:
   a) from about 10% to about 70% by weight of peroxodisulphate(s),
   b) from about 1% to about 14% by weight of percarbonate(s);
   c) from about 5% to about 15% by weight of disintegrant formed from cellulose-containing material,
   wherein the percarbonate(s) are included in the tablet core.

2. The bleaching tablet as claimed in claim 1, comprising from about 30% to about 40% by weight of peroxodisulphate(s).

3. The bleaching tablet as claimed in claim 1, wherein the peroxodisulphate(s) are an inorganic salt of a peroxosulphuric acid.

4. The bleaching tablet as claimed in claim 1, wherein the inorganic salt of a peroxosulphuric acid includes a mixture comprising from about 5% to about 40% by weight of potassium peroxodisulphate, from about 5% to about 20% by weight of ammonium peroxodisulphate and/or from 0 to about 10% by weight of sodium peroxodisulphate, respectively with respect to the total weight of the bleaching tablet.

5. The bleaching tablet as claimed in claim 1, wherein the peroxodisulphate(s) are included in the tablet shell.

6. The bleaching tablet as claimed in claim 1, wherein the bleaching tablet comprises from about 6% to about 14% by weight of disintegrant formed from cellulose-containing material.

7. The bleaching tablet as claimed in claim 1, wherein the percarbonate selected from an alkali metal, alkaline earth metal or ammonium salt of a percarbonate.

8. The bleaching tablet as claimed in claim 1, wherein the percarbonate is included in the bleaching tablet in a total quantity of from about 4% to about 12% by weight of the bleaching tablet.

9. The bleaching tablet as claimed in claim 1, comprising from about 25% to about 52.5% by weight of peroxodisulphate(s).

10. The bleaching tablet as claimed in claim 1, wherein the peroxodisulphate(s) are selected from the group of sodium peroxodisulphate, potassium peroxodisulphate, ammonium peroxodisulphate, or a mixture of these inorganic salts.

11. The bleaching tablet as claimed in claim 1, wherein the peroxodisulphate(s) comprise a mixture of potassium peroxodisulphate and ammonium peroxodisulphate.

12. The bleaching tablet as claimed in claim 1, wherein the peroxodisulphate(s) comprise a mixture of sodium peroxodisulphate and ammonium peroxodisulphate.

13. The bleaching tablet as claimed in claim 1, wherein the inorganic salt of a peroxosulphuric acid includes a mixture comprising from about 15% to about 30% by weight of potassium peroxodisulphate, from about 10% to about 15% by weight of ammonium peroxodisulphate and/or from about 2% to about 8.5% by weight of sodium peroxodisulphate, respectively with respect to the total weight of the bleaching tablet.

14. The bleaching tablet as claimed in claim 1, wherein the bleaching tablet comprises from 5% to 12.5% by weight of disintegrant formed from cellulose-containing material, wherein more than 90% by weight of the disintegrant is formed by a compacted granulate of the cellulose-containing material which has a particle size of from about 0.2 to about 6.0 mm.

15. The bleaching tablet as claimed in claim 1, wherein the percarbonate is sodium percarbonate and is included in the bleaching tablet in a total quantity of from about 4% to about 12% by weight, with respect to the total weight of the bleaching tablet.

16. A bleaching tablet consisting of a tablet core and a tablet shell encasing the tablet core, wherein the bleaching tablet—with respect to its weight—comprises:
   a) from about 25% to about 52.5% by weight of peroxodisulphates, wherein the peroxodisulphates comprise a mixture of potassium peroxodisulphate, ammonium peroxodisulphate, and sodium peroxodisulphate;
   b) from about 4% to about 12% by weight of alkali metal, alkaline earth metal or ammonium salt of a percarbonate; and
   c) from about 5% to about 15% by weight of disintegrant formed from cellulose-containing material,
   wherein the percarbonate(s) are included in the tablet core and wherein the peroxodisulphates are included in the tablet shell.

17. The bleaching tablet as claimed in claim 15, comprising from about 5% to about 40% by weight of potassium peroxodisulphate, from about 5% to about 20% by weight of ammonium peroxodisulphate, and from about 2 to about 8.5% by weight of sodium peroxodisulphate, respectively with respect to the total weight of the bleaching tablet.

18. The bleaching tablet as claimed in claim 16, wherein the inorganic salt of a peroxosulphuric acid includes a mixture comprising from about 15% to about 30% by weight of potassium peroxodisulphate, from about 10% to about 15% by weight of ammonium peroxodisulphate and/or from about 2% to about 8.5% by weight of sodium peroxodisulphate, respectively with respect to the total weight of the bleaching tablet.

19. A method for bleaching human hair, in which
   (a) the bleaching tablet as claimed in claim 1 is introduced into a quantity of water,
   (b) the mixture obtained from (a) is homogenized, and
   (c) the homogenized mixture from (b) is applied to the human hair.

* * * * *